(12) United States Patent
Aizenfeld et al.

(10) Patent No.: US 8,152,716 B2
(45) Date of Patent: Apr. 10, 2012

(54) VERSATILE CONTROL SYSTEM FOR SUPPLYING FLUID MEDIUM TO ENDOSCOPE

(75) Inventors: Amram Aizenfeld, Menashe (IL); Victor Levin, Haifa (IL); Golan Salman, Tirat Hacarmel (IL); Omer Shezifi, Haifa (IL); Dan Oz, Even Yehuda (IL); Avi Levy, Herzylia (IL)

(73) Assignee: Stryker GI Ltd., Haifa (IL)

( * ) Notice: Subject to any disclaimer, the term of this patent is extended or adjusted under 35 U.S.C. 154(b) by 1120 days.

(21) Appl. No.: 11/736,250

(22) Filed: Apr. 17, 2007

(65) Prior Publication Data
US 2007/0238929 A1 Oct. 11, 2007

Related U.S. Application Data

(63) Continuation-in-part of application No. 11/207,092, filed on Aug. 18, 2005, now Pat. No. 7,824,329.

(51) Int. Cl.
*A61B 1/12* (2006.01)
(52) U.S. Cl. .................... 600/158; 600/156; 600/159
(58) Field of Classification Search .................. 600/101, 600/118, 132, 136, 153, 155–159; 604/19, 604/23, 24, 26, 173
See application file for complete search history.

(56) References Cited

U.S. PATENT DOCUMENTS

| | | | | |
|---|---|---|---|---|
| 5,133,336 A * | 7/1992 | Savitt et al. | | 600/132 |
| 5,191,878 A * | 3/1993 | Iida et al. | | 600/157 |
| 5,343,855 A * | 9/1994 | Iida et al. | | 600/157 |
| 5,431,150 A * | 7/1995 | Yabe et al. | | 600/121 |
| 5,609,563 A * | 3/1997 | Suzuki et al. | | 600/118 |
| 6,485,409 B1 | 11/2002 | Voloshin | | |
| 2001/0039370 A1 * | 11/2001 | Takahashi et al. | | 600/159 |
| 2005/0004511 A1 * | 1/2005 | Figley et al. | | 604/23 |
| 2005/0119527 A1 * | 6/2005 | Banik et al. | | 600/117 |
| 2006/0049210 A1 * | 3/2006 | Larsen et al. | | 222/383.1 |

FOREIGN PATENT DOCUMENTS
WO WO2004/016299 7/2007

OTHER PUBLICATIONS

Bretthauer, M., et al. "NORCCAP (Norwegian colorectal cancer prevention): a randomised trial to assess the safety and efficacy of carbon dioxide versus air insufflation in colonoscopy." Gut vol. 50, Issue 5, pp. 604-607. May 2002. British Medical Assn., England.
Woltjen, J. "A retrospective analysis of cecal barotrauma caused by colonoscope air flow and pressure." Gastrointestinal Endoscopy, vol. 61, Issue 1, pp. 37-45. Elsevier Publishers.

* cited by examiner

*Primary Examiner* — Matthew J Kasztejna
(74) *Attorney, Agent, or Firm* — The Nath Law Group; Susanne M. Hopkins

(57) ABSTRACT

The present invention relates generally to the field of endoscopy and specifically to endoscopic apparatus used for endoscopic procedures during which a flexible tube is inserted into the rectum and colon for examination of the colon interior for abnormalities. More particularly, the present invention refers to a control system for supplying a fluid medium, e.g. air, carbon dioxide, water, to the endoscope.

18 Claims, 6 Drawing Sheets

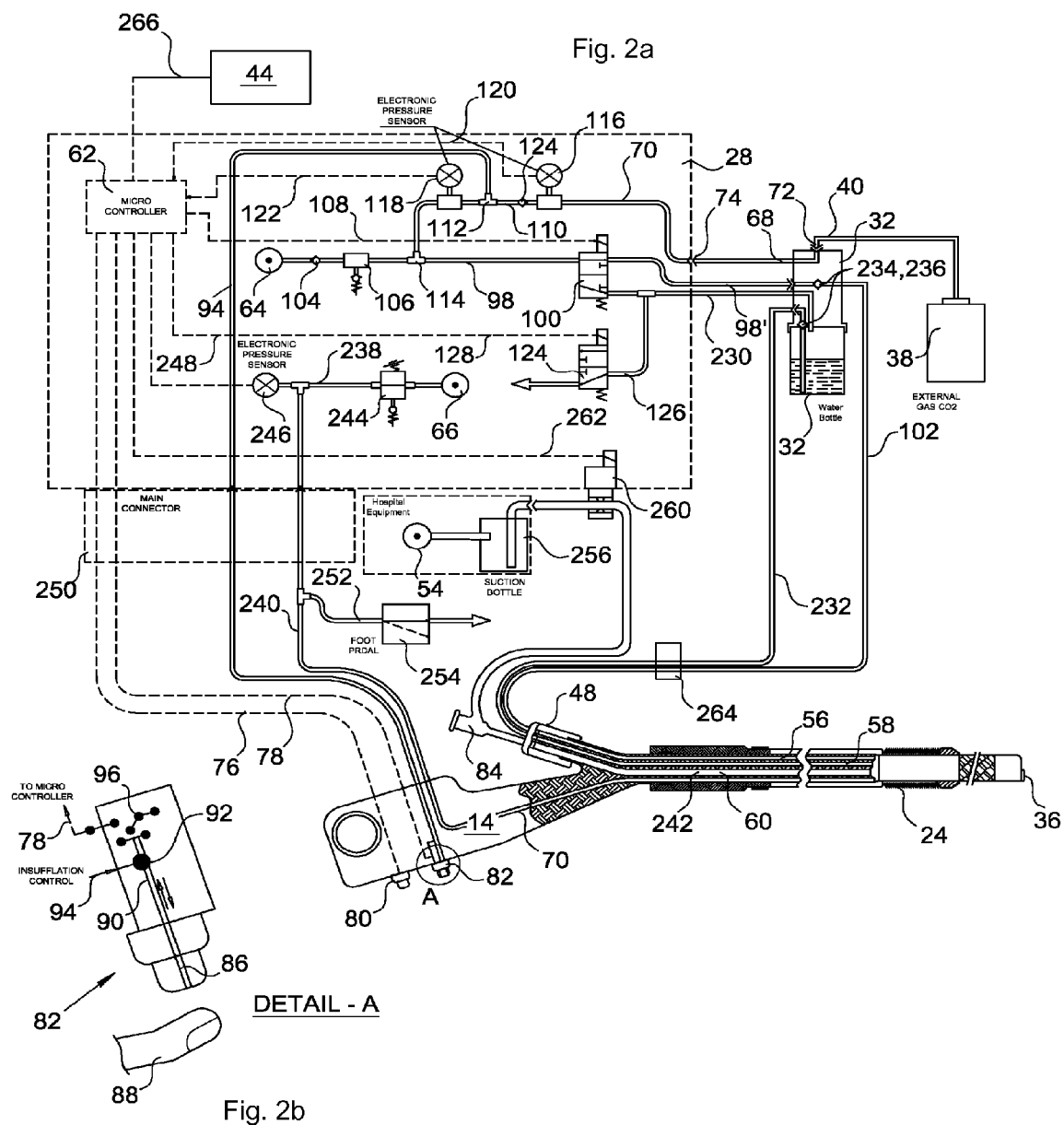

VERSATILE CONTROL SYSTEM FOR SUPPLYING FLUID MEDIUM TO ENDOSCOPE

CROSS-REFERENCE TO RELATED APPLICATIONS

This application is a continuation in part application of application Ser. No. 11/207,092, filed Aug. 18, 2005, and published on Mar. 9, 2006 as US 2006/0052665.

BACKGROUND OF THE INVENTION

1. Field of the Invention

The present invention relates generally to the field of endoscopy and specifically to endoscopic apparatus used for endoscopic procedures during which a flexible tube is inserted into the rectum and colon for examination of the colon interior for abnormalities. More particularly, the present invention refers to a control system for supplying a fluid medium, e.g. air, carbon dioxide, water, to the endoscope.

2. Summary of the Prior Art

Endoscopes employing inflatable flexible sleeves for propulsion of the endoscope within a patient's colon are known in the art. Voloshin (U.S. Pat. No. 6,485,409) discloses an endoscope with an endoscopic probe, a bending section for directing the probe within the colon (steering unit), an insertion tube and a flexible covering sleeve or a sheath, which is coupled proximally to the probe. The sleeve is attached to the endoscope in such a manner that its folded section is retained between a cap and an internal spindle, which are located at the rear part of the probe. When inflated, the folded section unfolds over a flange of the internal spindle and an inner portion of the sleeve is pulled behind the steering unit in a distal direction.

Eizenfeld (WO 2004/016299; International application PCT/IL2003/000661) describes an endoscope employing a flexible inflatable sleeve, which before inflation is retained within a dispenser. The dispenser employed in this endoscope has entry and exit ports, defining a transit passage through which the endoscope may pass. The dispenser is adapted to capture the sleeve as the endoscope is retracted through the transit passage in a proximal direction. In another embodiment, the dispenser includes an external sleeve fixed to the dispenser and this external sleeve is adapted to be extended from the dispenser when the endoscope is retracted, so that the external sleeve covers the flexible sleeve. By virtue of this provision any contamination on the flexible sleeve is retained within the external sleeve and does not contact the endoscope or any other objects or areas outside the patient's body. After the endoscope has been removed entirely from the flexible sleeve, the dispenser together with the external sleeve and flexible sleeve is discarded.

It is mentioned in the above reference that the endoscope is provided with an internal sleeve, which is also known as a multi-lumen tubing, since it is usually fitted with appropriate passages or lumens as required for irrigation, ventilation, suction and for passing endoscopic tools there through. The proximal end of the multi-lumen tubing is detachably connected via a dedicated connector, or so called hub, to a source of fluid medium and vacuum. A fluid control system is provided, which comprises an external control unit with a pump for supplying compressed air, a flask for supplying water and a pump for producing vacuum. The control unit is provided also with several pinch valves, which control the supply of the compressed air, water and vacuum to the multi-lumen tubing and compressed air to the inflatable sleeve.

As taught in the parent application Aizenfeld (US 2006/0052665), there is disclosed a new and improved control system and system control unit for supplying fluid medium to the multi-lumen tubing and/or to the inflatable sleeve of an endoscope provided with such a sleeve. This endoscope comprises an operation handle and an insertion tube provided with an insufflation channel, an irrigation channel and a suction channel extending there-along. There is a system control unit with at least one source of a first fluid medium, a source for a second fluid medium, and a source for a vacuum. Optionally, a multifunctional connector may be used for bringing the operation handle in fluid and electrical communication with the system control unit. The at least one source of a first fluid medium and the source for the second fluid medium are simultaneously connectable to and disconnectable from the insufflation channel and the irrigation channel. Compressed air is the first fluid medium for insufflation and water is the second fluid medium for irrigation. The compressed air may come from one or more compression pumps.

The use of compressed air during endoscopy does, however, have potential risks. The consequences of barotraumas caused during colonoscopic procedure are well documented; see for example article "A retrospective analysis of secal barotraumas caused by colonoscope air and pressure", Gastrointestinal Endoscopy, 2005, volume 61, No. 1, 37-45. Accordingly, it is advantageous to use less compressed air, so as to better control any risk of barotraumas.

It is known that the use of carbon dioxide gas can minimize those risks, otherwise presented by the use of compressed air. The teaching of *NORCCAP: a randomized trial to assess the safety and efficacy of carbon dioxide versus air insufflations in colonoscopy*, M Bretthauer, Gut, 2002; 50 604-607, are incorporated in its entirety herein by reference and it discusses the use of carbon dioxide gas instead of compressed air. Using carbon dioxide causes less patient discomfort and is safer during electrosurgical procedures.

SUMMARY OF THE INVENTION

A disadvantage of the device of the parent application is that it is designed to operate solely with compressed air and is not suitable for the inclusion or use of compressed carbon dioxide gas during insufflation, and it operates with compressed air and its attendant risks.

Thus it is an object of the present invention to improve upon the control system of the parent application and provide a new and improved control system and system control unit for supplying fluid medium to the multi-lumen tubing and/or to the inflatable sleeve of an endoscope provided with such a sleeve, wherein, the control system is suitable to control supply of not only compressed air, but also of carbon dioxide.

It is a further object of the present invention to provide a new and improved system and system control unit, which is convenient and simple in operation and maintenance.

Yet another object of the present invention is to provide a new and improved control system and system control unit, which allows the use either of compressed air or of carbon dioxide gas for insufflation and for irrigation and of compressed air for inflating the sleeve.

For a better understanding of the present invention as well of its benefits and advantages, reference will now be made to the following description of its embodiments taken in combination with the accompanying drawings.

BRIEF DESCRIPTION OF THE SEVERAL VIEWS OF THE DRAWINGS

FIG. 2a depicts the control system and system control unit of the present invention.

FIG. 2b is an enlarged view of a control button.

DETAILED DESCRIPTION OF THE PREFERRED EMBODIMENT

Figure 1:
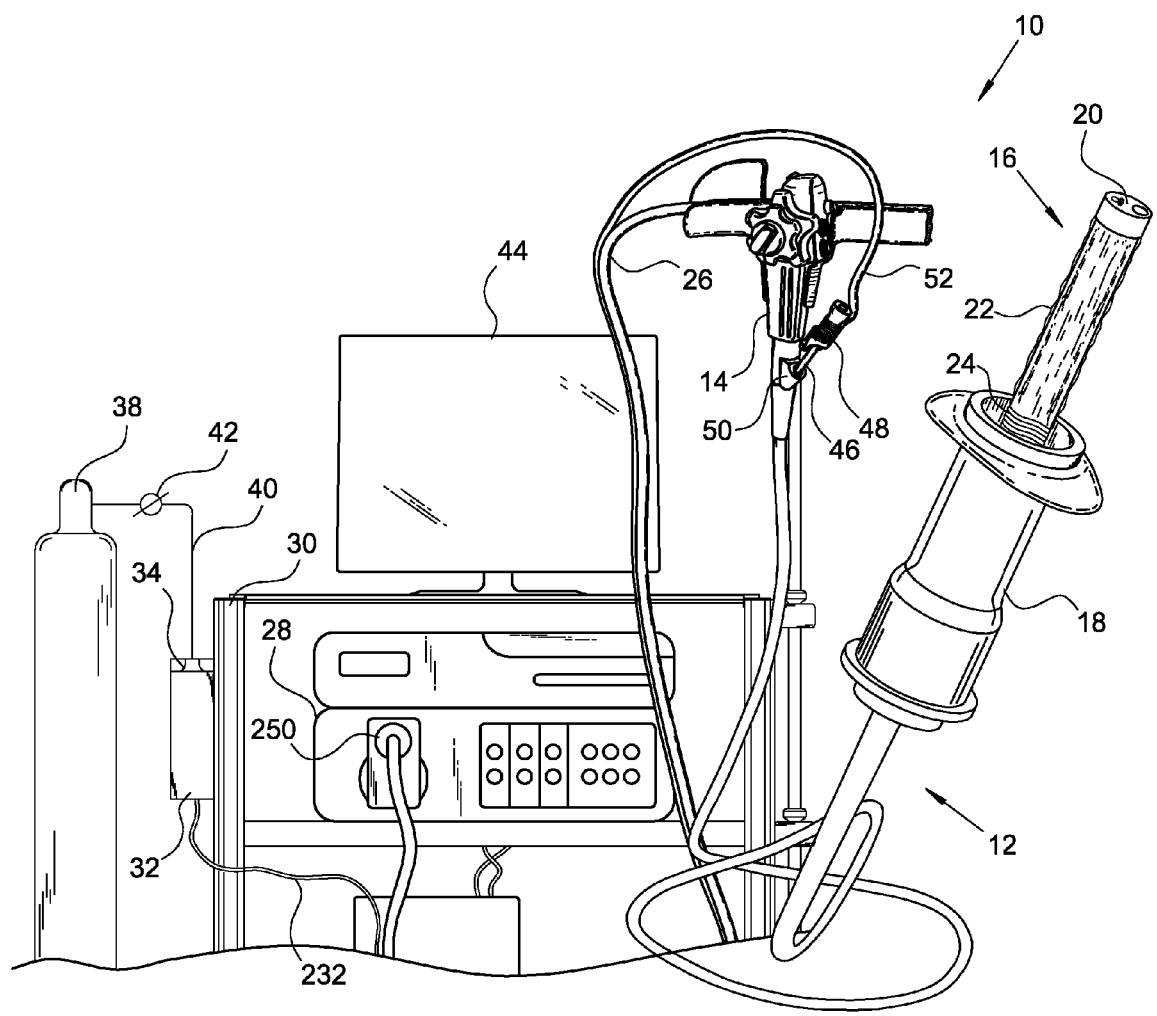
FIG. 1 depicts a general view of an endoscopic apparatus employing the control system of the present invention.

With reference to FIG. 1 an endoscopic apparatus, preferably a colonoscopic apparatus 10, is shown with the following main components. The apparatus comprises an endoscope having an insertion tube with its proximal section 12 connected to an operation handle 14 and with its distal section 16 inserted in and protruding from a disposable dispenser 18 in which a disposable inflatable covering sleeve is stored in a folded state before the endoscopic procedure and from which the sleeve feeds out during the endoscopic procedure. An optical head 20 for viewing the interior of the body channel is provided at the distal end of the insertion tube. An example of such an endoscopic apparatus and general explanation of its construction and functioning can be found in Eizenfeld (WO 2004/016299; International application PCT/IL2003/000661), which is herein incorporated by reference.

It is also shown in FIG. 1 that a disposable inflatable sleeve covers the distal region of the endoscope. This sleeve comprises a frontal non-inflatable portion 22 and a rear folded portion 24. The frontal portion covers the distal section of the endoscope, and does not inflate when the endoscope advances within the colon. The rear portion covers the insertion tube and unfolds from the dispenser when compressed air or other fluid medium inflate the sleeve. By virtue of this provision, the endoscope is propelled within the body passage. The endoscope, which can be used with the control system of the present invention, can be of similar type in the sense that it employs the same propelling mechanism, which is based on inflation of the flexible sleeve coupled to the endoscope's distal section. It should be appreciated, however, that the present invention is not limited merely to the colonoscopy field as such or to endoscopes, which are propelled by an inflatable sleeve. It can be employed in any other endoscopic apparatus used for medical procedures requiring insertion of a probe in a body passage for inspection of its interior.

FIG. 1 also depicts an operating handle 14 which is connected by an umbilical cord 26 to a system control unit (SCU) 28, which is deployed on a cart 30.

Also proximate to the SCU 28 and attachable to the cart is a flask 32, filled with water, to be supplied under pressure for irrigation of a window for optical lens provided at the distal end of the optical head. The flask is closed by a detachable cover 34 and is in fluid communication with the SCU and with a sprinkler provided at the distal end of the insertion tube. The sprinkler is designated by reference numeral 36 and is shown in FIG. 2a.

As shown in FIG. 1, proximate to the cart there is provided a source of compressed carbon dioxide gas. This source can be for example a cylinder 38, which is in fluid communication with the SCU via a line 40 passing through the flask cover. A pressure regulator 42 can be provided in the line 40 for reducing the carbon dioxide pressure to the required level of about 0.5 bar before carbon dioxide enters the SCU. As will be explained further the system control unit of the invention is versatile in the sense that it may use either compressed air or compressed carbon dioxide gas for insufflation of the colon and for irrigation of the window provided at the optical head. The source of this pressure is either compressed air or compressed carbon dioxide.

As seen in FIG. 1 the apparatus is provided with a monitor 44, which is suitable to display images of the body channel viewed by the optical head as well as various information associated with functioning of the control system.

One should also bear in mind that within the insertion tube are provided various devices, which are necessary for functioning of the colonoscopic apparatus. These devices are known per se. Among such devices are, for example, vertebrae and strings, which can be manipulated by the operation handle. It should be appreciated, that along the colonoscope extends a multi-lumen tubing with appropriate passages for supplying water, as required for irrigation of the colon, carbon dioxide (and sometime air) as required for insufflation and vacuum as required for suction. The multi-lumen tubing also allows introduction of surgical instruments into the colon as might be required during the colonoscopic procedure.

The multi-lumen tubing extends through the entire length of the insertion tube, passes the handle and its proximal end 46 is connected to a dedicated connector 48, which is detachably connectable to a lateral port 50 provided on the handle. The connector connects the proximal end of the multi-lumen tubing with so-called multichannel 52 extending along the umbilical cord. It will be explained further with reference to FIG. 2a, that the multichannel is fitted with tubes through which fluid media (water, air, carbon dioxide) and vacuum can be supplied from the SCU to the multi-lumen tubing. This arrangement is disclosed in Bar-On (WO 2005/110200; International application PCT/IL2005/000428). It will be also shown further with reference to FIG. 2a that appropriate channels are provided in the multilumen tubing. These channels are in fluid communication with respective tubes of the multichannel.

In practice the multi-lumen tubing, the multichannel and the connector are manufactured from plastic material. It is advantageous if they are cheap, disposable items, which are discarded at the end of the endoscopic procedure after the colonoscope has been evacuated form the body passage. By virtue of this provision, preparation for a new colonoscopic procedure is simple, convenient and fast and it is not associated with spreading of any contamination picked up from the body passage during the previous endoscopic procedure.

Referring now to FIG. 2a a preferred embodiment of the fluid control system of the invention is seen. The system has as a main component, i.e. the SCU 28, designated by a dotted line, which schematically delimits the SCU housing. The SCU controls supply of compressed air or carbon dioxide, water and vacuum as required for proper functioning of the colonoscopic apparatus 10. Some external components of the fluid control system, namely cylinder 38 of carbon dioxide, flask 32 of water, vacuum pump unit 54 and monitor 44 are also seen. In practice the flask volume should be sufficient to contain about 300 cc of water. As a suitable source of vacuum one could optionally use available hospital equipment capable of producing a vacuum of about −(0.3-0.5 bar), preferably −0.4 bar to enable suction from the body passage through the multi-lumen tubing. The vacuum pump should be capable to provide a flow rate of at least 20 liter per minute.

A portion of the multi-lumen tubing extending along the operating handle is also seen in FIG. 2a. The multi-lumen tubing is provided with channels 56, 58 and 60, which are respectively dedicated to supply air (or carbon dioxide), water and vacuum.

Within the SCU are provided the necessary electronic, pneumatic and hydraulic components, e.g. a logic unit 62, first and second pumps 64, 66 for producing compressed air, and various solenoids and valves as will be further explained. The logic unit comprises a microcontroller. It is not shown specifically, but should be appreciated that appropriate power supply means is also provided within the SCU as required for activation of the valves, pumps, solenoids and energizing the logic unit.

Externally positioned near the housing of the SCU is a cylinder 38, providing a supply of compressed carbon dioxide at a pressure of about 0.5 Bar. The cylinder is detachably connectable to the cover 34 of the flask 32 via external line 40 and then to the SCU via line 68. A line 70 is provided in the SCU for fluid communication between the SCU and the line 68. The compressed carbon dioxide is supplied to the SCU through line 68 and then through line 70. A first connector 72 and a second connector 74 are provided for fast detachable connecting of the cylinder with the cover and of the cover with the SCU. By virtue of this provision the cylinder can be brought in fluid communication with the SCU. The cover and the flask could be disposable. They can be designed as separate items or as a set suitable for supplying to the multilumen tubing the necessary fluid medium, which is either air, or carbon dioxide, or water or vacuum. In FIGS. 4-8 are presented various embodiments of the cover and a versatile connector member. These will be described later on.

The logic unit is electrically connected by signal lines 76, 78 to respective control buttons 80, 82 provided at the operating handle. The button 80 enables controlling of suction through channel 60 made in the multi-lumen tubing. This channel functions either as a suction channel (when vacuum is supplied there through) or as a working channel when it is required to insert a surgical tool through a port 84. The button 82 enables supply of compressed air or compressed carbon dioxide gas to the body passage through a dedicated insufflation channel 56. This button also enables supply of water to the distal end of the endoscope or to the body passage through a dedicated irrigation channel 58 and sprinkler 36. A through going opening 86 is provided in the button 82. This opening can be closed or opened by the doctor's finger 88 during operation of the handle. The through going opening is in flow communication with a button mechanism, which resides in the button 82. In FIG. 2b the button mechanism is presented schematically. A cross-section of the button mechanism is presented in FIG. 3.

Figure 3A:
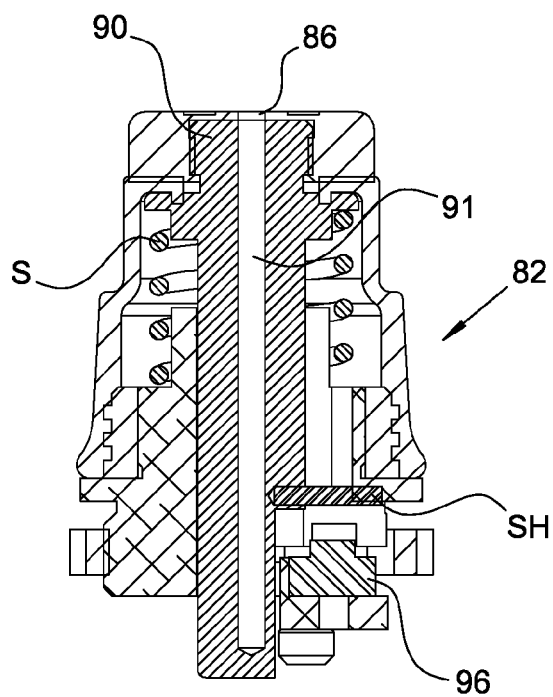
FIGS. 3a and 3b depict a cross-sectional view of the control button.
Figure 3B:
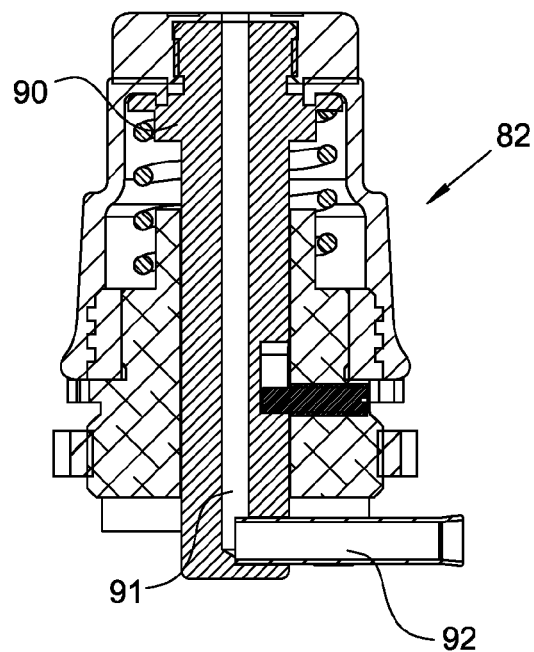

As seen in FIGS. 3a and 3b the button mechanism comprises a hollow pin 90, biased by a spring S, wherein the pin is linearly displaceable with respect to the operating handle when the doctor's finger presses the button. The through going opening 86 extending along the button is in flow communication with a duct 91 provided in the pin 90 and with a lateral duct 92. The aperture is in fluid communication with an insufflation control line 94 through which compressed air or compressed carbon dioxide gas proceeds from the SCU to the operating handle and can be released to the atmosphere through the control button 82 when the opening 86 is open. Upon closing the opening 86 the pressure in the line 94 raises and this triggers supply of compressed air from the first pump 64 or compressed carbon dioxide gas to the insufflation channel 56. At one end of the pin there is provided a micro switch 96, which is actuatable by a shoulder SH, provided laterally at the pin such that the micro switch can close or open a circuit between the signal line 78 and the logic unit 62. The micro switch is actuated when the pin is forcibly displaced by pressing the button. As will be explained further by closing and opening of the opening 86 as well as by displacement of the pin 90 one could trigger either the insufflation or the irrigation mode. When the opening is closed, but the button is not pressed the insufflation mode is initiated. When the button is pressed to displace the pin the irrigation mode is initiated.

The components residing within the SCU refer to two main lines for supplying fluid media to the channels of the multi-lumen. The first line is responsible for insufflation or irrigation and it allows supply of compressed air from the first pump 64, or compressed dioxide gas from cylinder 38 or water from flask 32. The second line is responsible for inflating the sleeve and allows supply of compressed air from the second pump 66. The first pump is preferably controllable by a stepped variation of the voltage supplied thereto so to produce flow of 2-3 l/min at zero pressure or flow of 1.5 l/min at 0.4 bar pressure. These values correspond to those required for insufflation. In other words the pump is deliberately selected in such a manner that its characteristics limit the flow up to certain range and by variation of the voltage supplied to the pump it is possible to vary the flow within the required range.

The control system further is provided also with a third line for supplying vacuum from the pump 54 to the suction channel 60.

Referring to FIG. 2a the first supply line comprises the first pump 64, an internal supply line 98, a first solenoid valve 100 and an internal supply line 98'. The exit port of the line 98' is in fluid communication with an external channel 102 of the multichannel 52 and is in fluid communication with the insufflation channel 56 via connector 48.

The first supply line further comprises a check valve 104 and a safety valve 106 located in series after the first pump. The check valve prevents back flow from the line 98 to the pump 64. The check valve should be selected to create pressure drop of about 0.25 psi. and the safety valve should be selected in order to keep pressure in the system below 0.5 bar.

The compressed air produced by the first pump proceeds via an internal supply line 98, then via the solenoid valve 100, via an internal supply line 98' and finally via an external supply line 102 to the insufflation channel 56. The solenoid valve 100 is in electric communication with the logic unit through a signal line 108.

The first supply line further comprises a carbon dioxide supply branch 110. This branch is in fluid communication with the line 70 as well as with the internal supply line 98 via a knee 112 and with the insufflation control line 94 via a knee 114. The carbon dioxide supply branch is provided with a first electronic pressure sensor 116 and with the second electronic pressure sensor 118, which are respectively disposed at right and left side of the knee 114. Both pressure sensors are in electric communication with the logic unit by respective signal lines 120, 122. The pressure sensors should be capable to measure pressure in the range of up to 1 bar with accurateness of 1-2%.

A check valve 124 is provided in the carbon dioxide supply branch. The check valve is preferably located between the first pressure sensor and the knee 114. The check valve prevents back flow from the SCU to the cylinder and it should create pressure drop of about 0.25-0.5 psi.

The compressed carbon dioxide is supplied from cylinder 38 via lines 40, 70 and then through the carbon dioxide branch and knee 112 to internal supply line 98, and then through solenoid valve 100, internal supply line 98' and external channel 102 to the insufflation channel 56.

The first supply line further comprises a second solenoid valve 124, which can be brought in fluid communication with the first solenoid valve 100 via a line 126 and with atmosphere. The second solenoid valve is in electric communication with the logic unit 62 via a signal line 128. The first solenoid valve is in fluid communication with the flask 32 by a line 230. The flask is in fluid communication with the irrigation channel 58 via a channel 232, which is part of the multichannel 52. There are provided also two check valves 234,236, which are respectively installed in the channel 232 and in the line 102. These check valves prevent entering of contamination from the body interior to the SCU. Apart of the above the check valves eliminate a possibility that a doctor will inadvertently activate the insufflation and irrigation when this is not necessary. The valves should be selected in such a manner that they establish a pressure drop of about 1-0.5-2 psi, which is sufficient for eliminating the inadvertent activation. The first supply line should provide insufflation flow of about 1-2 l/min, preferably 1.1-1.8 l/min and irrigation flow of about 1-1.5 cc/sec, preferably 1.3 cc/sec. The insufflation flow rate is controllable in accordance with the user's requirements.

The second supply line comprises second pump 66, which is in fluid communication via a line 238 with an external channel 240. This channel is in fluid communication with the operating handle 14 and with an inflating channel 242 extending along the insertion tube. Through this channel compressed air is supplied for inflating folded portion 24 of the sleeve. The second supply line further comprises a safety valve 244 and an electronic pressure sensor 246, which is in electric communication with the logic unit 62 via a signal line 248. The second pump should produce flow of compressed air of 8 l/min at zero pressure or flow of 5 l/min at 0.4 bar pressure. The safety valve should limit the pressure in the system under 0.6 bar.

For connecting the SCU with external lines 94, 240 supplying the fluid media as well as with signal lines 76, 78 a detachable multifunctional connector 250 is provided. This connector is multifunctional in the sense that it enables not only passing electrical signals between the SCU and the control buttons at the operating handle, but also ensures supplying of compressed air from pumps 64, 66 or compressed carbon dioxide gas from cylinder 38 to the operating handle 14. There is provided also a branch 252 in the main connector, which brings in fluid communication a portion of the channel 240 extending along the connector with a foot pedal 254, which is outside the SCU. The pedal is configured as normally opened switch in the sense that when the pedal is not pressed the compressed air produced by the second pump is released to the atmosphere via line 238, branch 252 and the pedal. Upon pressing the pedal the compressed air proceeds to the external line 240 and then to the handle 14 and to the inflating channel 242.

The line for supplying vacuum comprises vacuum pump 54 or any other available source of vacuum and a suction bottle 256, which is detachably connectable with a vacuum supply channel 258. The channel 258 passes via a pinch valve 260 provided at the SCU to supply vacuum in a controllable fashion to the suction channel 60. The pinch valve is in electric communication with the logic unit via a signal line 262.

The channel 258 is also a part of the multichannel and it is seen in FIG. 2a that channels of the multi-lumen tubing are in flow communication with the respective channels of the multichannel by virtue of connector 48 provided at the lateral port 50 of the handle. The channels 258, 232 and 102 respectively supply vacuum to the suction channel 60, water to the irrigation channel 58 and compressed air or compressed carbon dioxide to the insufflation channel 56. In accordance with one of the aspects of the present invention, channels for water and compressed air 232, 102 are immediately connectable and disconnectable to the respective sources of the fluid media by a common connector 264 without the necessity to connect/disconnect the channels one by one by separate connectors dedicated to each line. This provision renders the set up of the system very simple, convenient and fast. It is not shown specifically, but should be appreciated that, the common connector could be arranged at the flask itself or at its cover.

The logic unit is electrically connected by a line 266 with the monitor 44 on which are displayed inter alia current working parameters of the SCU and its mode of operation.

The control system depicted in FIG. 2a operates as follows. Before activation of any of the desired modes (insufflation, irrigation, suction, inflating) the SCU is turned on and its all relevant components are energized.

When it is required to inflate the sleeve one should press foot pedal 254. Upon pressing the pedal a signal is transferred to the logic unit, which, in its turn, generates a control signal that allows compressed air from pump 66 to enter the sleeve via external channel 240, along the handle and then via inflating channel 242 in the insertion tube. In order to release the pressure from the sleeve, one should release the foot from the pedal. This releases the compressed air produced by pump 66 to the atmosphere via branch 252 and then via the pedal.

When suction is required, one should press control button 80. Upon pressing this button, a control signal will be generated by the logic unit to open pinch valve 260 and then vacuum will be allowed to proceed to the body cavity via vacuum supply channel 258 and via suction channel 60 extending along the insertion tube.

For insufflation by carbon dioxide, one should connect the cylinder with the bottle cover 34 such that fluid communication would be established between cylinder 38, line 40, line 68 and line 70. As soon as carbon dioxide enters in the SCU the first electronic pressure sensor, which is located at the entrance of the carbon dioxide, detects presence of the carbon dioxide and produces a logic signal, which proceeds to the logic unit. The logic signal is transformed by the logic unit into a control signal that turns off the pump 64. Carbon dioxide proceeds from line 70 via knee 112 to the control line 94 and via knee 114 to the internal supply line 98. The opening 86 at the control button 82 should be closed by a finger without however pressing the button 82. In this situation the solenoid valve 100 by default is in the position, in which fluid communication is allowed between the internal supply lines 98 and 98' as well as external supply line 102 and carbon dioxide is allowed to proceed to the insufflation channel 56. The second pressure sensor senses the current pressure of carbon dioxide being supplied for insufflation. The value of the supplied pressure is send by the logic unit to monitor 44, where it is displayed along with a notice that the SCU operates in the insufflation mode. Check valve 104 prevents back flow of air from the SCU.

For effecting mode of irrigation one should deeply press the control button 82. This causes the micro switch 96 to close a circuit with the signal line 78. Then a control signal is activated by the logic unit and sent to the solenoid valve 100. This signal puts the solenoid valve in a position, in which fluid communication is possible between line 98 and line 230. Accordingly compressed carbon dioxide is allowed to proceed from the cylinder via lines 40, 68, 110, 98 and 230 to the water flask and to urge water to proceed via channel 232 to the irrigation channel 58 until it is ejected via sprinkler 36 to the window of the optical head. In practice it is sufficient if water is supplied for irrigation with a flow of about 1.3 cc per second.

So long as pressurized carbon dioxide is being supplied to the flask the second solenoid valve 124 is in the position, in which it does not communicate with the atmosphere to prevent release of carbon dioxide through line 126 and then through the solenoid valve 124. Monitor 44 displays current pressure of carbon dioxide sensed by pressure sensor 118 along with a notice that the SCU operates in the irrigation mode.

When it is required to terminate the irrigation one should release the control button 82. This causes generation of a control signal, which puts the solenoid valve 124 in a position, in which it communicated with the atmosphere and thus remaining in the flask pressurized carbon dioxide can be released to atmosphere via line 230, line 126 and then via solenoid valve 124.

The advantage of using two solenoid valves instead of one lies in the fact that miniature components with lesser amount of ports can be employed thus rendering the whole system more compact. At the same time there is no need to increase the amount of logic signals.

For insufflation by air one should disconnect the cylinder 38 from the SCU and close the opening 86, without however pressing the control button 82. In this situation solenoid valve 100 is in a position, in which flow communication is established between line 98 and 98'. Pump 64 remains be turned on and produces compressed air, which proceeds through lines 98, 98' and 102 to the insufflation channel. In practice the pump should be capable to produce an air flow of about 1.5 liter per minute at a pressure of about 0.4 bar. It is advantageous if this capacity becomes available when a nominal voltage is supplied to the pump. To control the air flow one can vary the nominal voltage. It would be beneficial if the nominal voltage is stepwise reducible to enable control of the air flow. In practice three steps of voltage would be selectable, i.e. 70%, 85% and 100% of the nominal voltage. At the same time pressure of compressed air in the line would be controllable by the safety valve 106.

When it is required to terminate the irrigation one should release the control button 82. This causes generation of a control signal, which puts the solenoid valve 124 in a position, in which it communicated with the atmosphere and thus remaining in the flask pressurized air can be released via line 230, line 126 and then via solenoid valve 124.

Thus by virtue of the SCU of the present invention both the insufflation and the irrigation mode can be carried out either by using of compressed carbon dioxide or compressed air.

Figure 4:
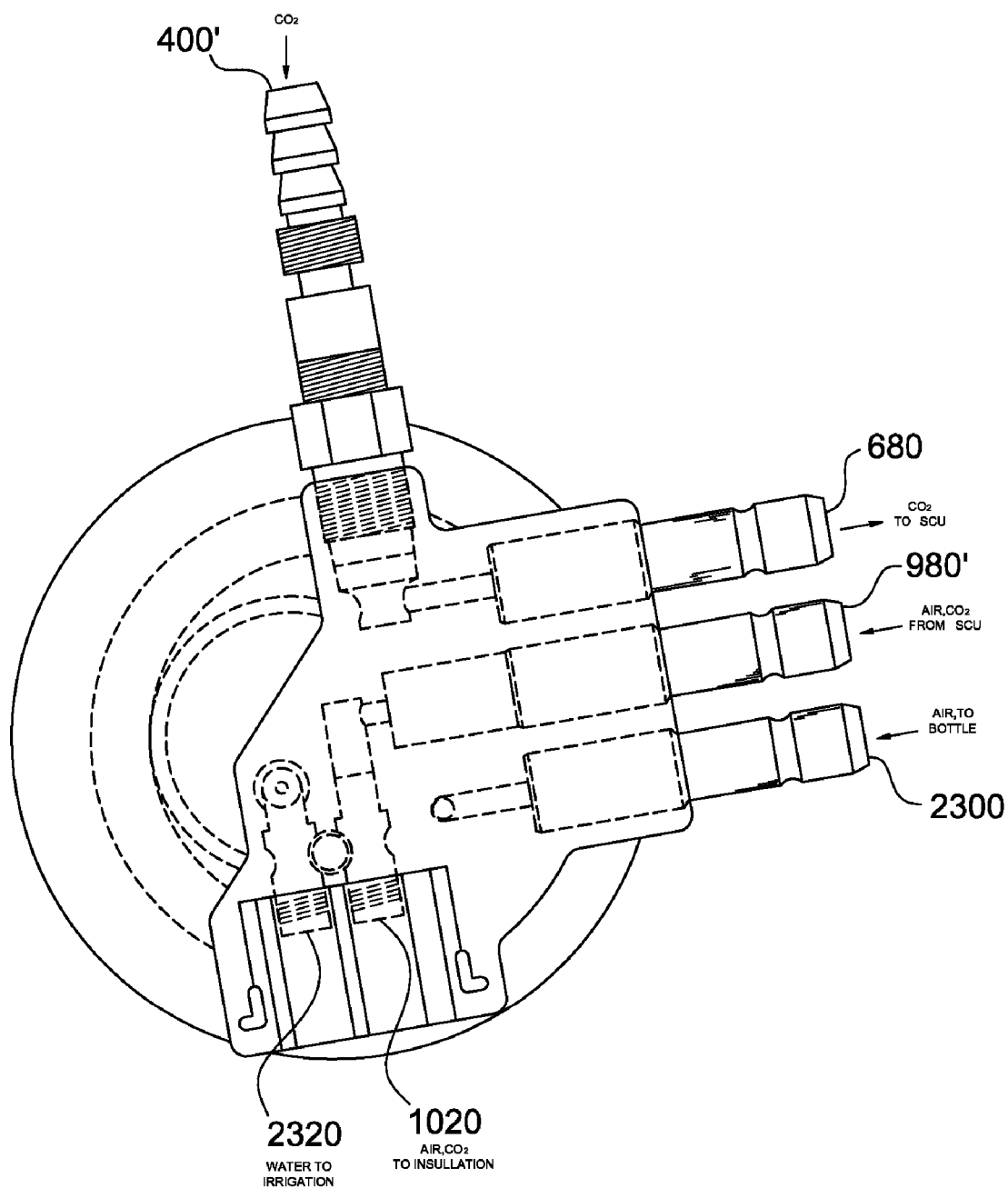
FIG. 4 shows a top view of the integral cove in a first embodiment of connecting the SCU with the flask and with the source of compressed carbon dioxide, wherein the connection is provided by virtue of an integral cover closing the flask.

Now with reference to FIGS. 4-7 various embodiments of connection the SCU with the flask will be described. In FIG. 4 is shown a first embodiment, in which connection is provided by virtue of an integral cover 34 closing the flask. FIG. 4 depicts a top view of the integral cover. Within the cover are made ducts, terminating by corresponding inlet and outlet ports for fluid communication with the channels, through which fluid medium is supplied to the SCU, from the SCU to the flask and from the cover to the multichannel. So, for example it is seen that the cover is provided with an inlet port 400, which is detachably connectable to the line 40 for supplying compressed carbon dioxide. The inlet port 400 is fluid communication with an outlet port 680, which is connectable to the line 68, through which the compressed carbon dioxide enters the SCU. Furthermore, the cover is provided with an inlet port 980' for connecting to the line 98', through which either compressed air, or compressed carbon dioxide is supplied from the SCU to the insufflation channel of the multichannel and then to multilumen. The inlet port 980' is in fluid communication with an outlet port 1020, which is connectable to the channel 102 of the multichannnel. The multichannel is connectable to the cover by the fast releasable connector 264. The cover is provided further with an inlet port 2300 for supplying compressed air to the bottle via line 230. The cover is provided also with an outlet port 2320 for connecting to the line 232 of the multichannel through which water is supplied to the irrigation channel in the multilumen. In a preferred embodiment check valves can be installed in ports 980' and 2320. Fluid communication between ports 2320, 1020 and the multichannel is enabled by virtue of entering the multichannel in a female part of the connector 264.

Figure 5:
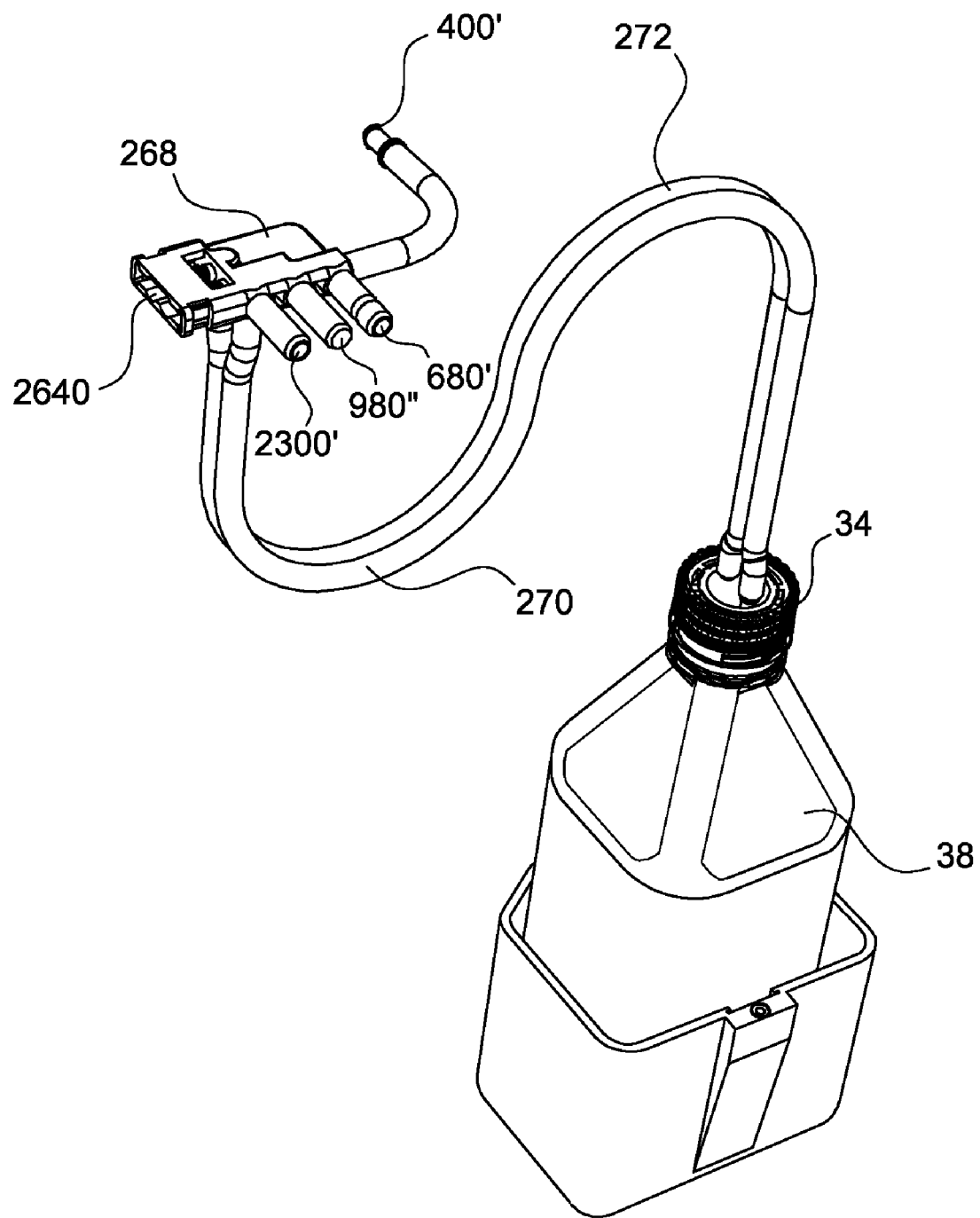
FIG. 5 shows an alternative embodiment of FIG. 4, wherein all inlet and outlet ports are located on a dedicated connection member, which is separate from the cover.

In FIG. 5 is shown an alternative embodiment, in which all inlet and outlet ports are located on a dedicated connection member 268, which is separate from the cover 34. In this embodiment fluid communication with the flask 38 is enabled through tubes 270, 272, which are connectable to the connection member through corresponding ports. The connection member is made of plastic, for example by injection molding and is configured as a plate with plurality of ports provided laterally at the upper side of the connection member. Two ports at the lower side of the connection member are provided for connecting with tubes 270, 272. So, for example it is seen that the connecting member is provided with an inlet port 400', which is detachably connectable to the line 40 for supplying compressed carbon dioxide. The inlet port 400' is in fluid communication with an outlet port 680', which is connectable to the line 68, through which the compressed carbon dioxide enters the SCU. Furthermore, the connection member is provided with an inlet port 980" for connecting to the line 98', through which either compressed air, or compressed carbon dioxide is supplied from the SCU to the insufflation channel of the multichannel and then to multilumen. The inlet port 98" is in fluid communication with an outlet port 1020', which is connectable to the channel 102 of the multichannnel. The multichannel is connectable to the appropriated ports of the connector by insertion in the female part 2640 of the fast releasable connector 264. The connecting member has an inlet port 2300' for connecting to the tube 270 for supplying compressed air to the bottle. The connecting member is provided also with an outlet port 2320' for connecting to the tube 272 for supplying water from the flask to the multichannel and then to the irrigation channel in the multilumen. In a preferred embodiment check valves can be installed in ports 980" and 2320'.

Figure 6:
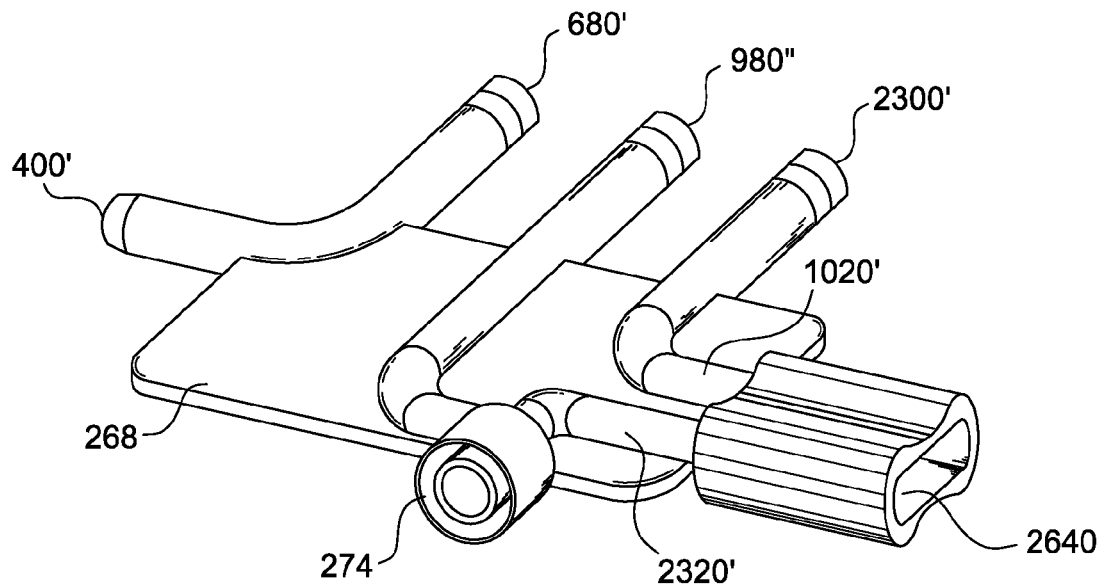
FIGS. 6 and 7 show various configurations of the connecting member.
Figure 7:
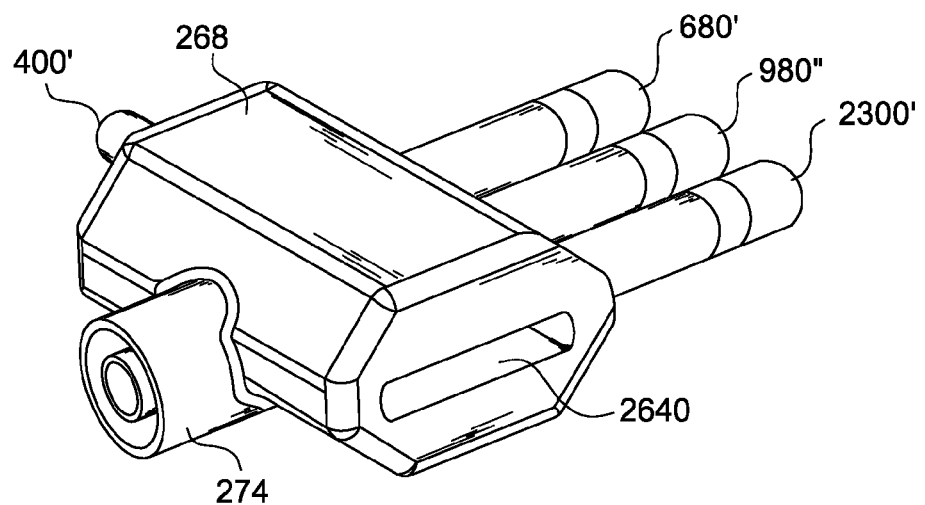

Referring to FIGS. 6 and 7 there are shown various configurations of the connecting member. The same reference numerals designate similar ports. In these embodiments the tubes 270, 272 are in fluid communication with the connecting member not via two separate ports, which are remote from each other but through a combined port 274 suitable for tube in tube disposition.

It should be appreciated that the invention is not limited to the above-described embodiments and that one of ordinary skill in the art can make modifications or changes without deviating from the scope of the invention, as will be defined in the appended claims.

It should also be appreciated that the features disclosed in the foregoing description, and/or in the following claims, and/or in the accompanying drawings may, both separately and in any combination thereof, be material for realizing the present invention in diverse forms thereof.

It should be further appreciated that the pressures and flow rates of various components are given as the preferred pressures and flow rates. Variations in these parameters may be made without affecting the usefulness of the present invention.

We claim:

1. A control system supplying a fluid medium to an endoscopic apparatus comprising an operation handle and an insertion tube, the control system comprising:
 a system control unit comprising
  a source of a first fluid medium,
  hydraulic and pneumatic components configured to facilitate fluid transmission of the first fluid medium to the insertion tube comprising an insufflation channel, an irrigation channel and a suction channel, each extending separately along the entire length of the insertion tube, and
  a logic unit configured to control the hydraulic and pneumatic components;
 a source of a second fluid medium, the source of the second fluid medium being detachably connectable to the system control unit to be in fluid communication therewith;
 a source of a third fluid medium in fluid communication with the irrigation channel;
 a vacuum source in fluid communication with the suction channel;
 a detachable connector effecting fluid communication between the operation handle of the apparatus and the system control unit, the detachable connector configured to attach and detach from the system control unit; and
 a multifunctional connector connecting fluid lines and signal lines with the system control unit.

2. A control system, according to claim 1, wherein the source of a first fluid medium comprises a carbon dioxide canister and the first fluid medium is compressed carbon dioxide gas.

3. The control system according to claim 2, wherein the operation handle comprises a control button provided with an opening, wherein upon closure thereof compressed carbon dioxide from the carbon dioxide canister is supplied to the insufflation channel.

4. The control system according to claim 3, wherein the control button comprises a hollow pin linearly displaceable with respect to the operating handle, and a spring biasing the hollow pin.

5. The control system according to claim 4, further comprising a micro switch positioned at one end of the hollow pin, and a shoulder within the operating handle provided laterally of the hollow pin and actuating the micro switch.

6. The control system according to claim 2, wherein the source of a second fluid medium consists of a flask with a detachable cover.

7. The control system according to claim 6, wherein the carbon dioxide canister is detachably connected to the detachable cover of said flask.

8. The control system according to claim 7, wherein the detachable cover includes ducts communicating with fluid lines.

9. The control system according to claim 8, wherein the detachable cover includes a dedicated connection member with the ducts.

10. The control system according to claim 6, wherein the detachable cover includes ducts communicating with fluid lines.

11. The control system according to claim 10, wherein the detachable cover includes a dedicated connection member with the ducts.

12. The control system according to claim 1, wherein the source of a first fluid medium further comprises a pump.

13. The control system according to claim 12, wherein the source for a first fluid medium further comprises a second pump.

14. The control system according to claim 1, wherein the insertion tube comprises a multi-lumen tubing and the insufflation channel, the irrigation channel and the suction channel extending along the multi-lumen tubing.

15. The control system according to claim 1, wherein the source of a second fluid medium consists of a flask with a detachable cover.

16. The control system according to claim 15, wherein the detachable cover includes ducts communicating with fluid lines.

17. The control system according to claim 16, wherein the detachable cover includes a dedicated connection member with the ducts.

18. The control system according to claim 1, further comprising pressure sensors in supply lines for the first fluid medium and in communication with the system control unit.

* * * * *